US008002778B1

(12) United States Patent
Meridew

(10) Patent No.: US 8,002,778 B1
(45) Date of Patent: Aug. 23, 2011

(54) CROSSPIN AND METHOD FOR INSERTING THE SAME DURING SOFT LIGAMENT REPAIR

(75) Inventor: Jason D Meridew, Syracuse, NY (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 462 days.

(21) Appl. No.: 10/878,559

(22) Filed: Jun. 28, 2004

(51) Int. Cl.
*A61B 17/86* (2006.01)

(52) U.S. Cl. .................. 606/104; 623/13.11; 623/13.14; 606/323; 606/321

(58) Field of Classification Search ................ 606/72, 606/104
See application file for complete search history.

(56) References Cited

U.S. PATENT DOCUMENTS

| | | | | |
|---|---|---|---|---|
| 461,621 | A | | 10/1891 | Rogers |
| 1,762,394 | A | * | 6/1930 | Hosking ...................... 411/306 |
| 1,940,878 | A | * | 12/1933 | Olson .......................... 411/306 |
| 2,640,521 | A | * | 6/1953 | Zavoico ....................... 411/258 |
| 2,695,607 | A | | 11/1954 | Hipps et al. |
| 3,832,931 | A | * | 9/1974 | Talan .......................... 411/80.2 |
| 3,871,379 | A | | 3/1975 | Clarke |
| 4,044,647 | A | * | 8/1977 | Takahashi ..................... 411/39 |
| 4,053,982 | A | * | 10/1977 | Weissman ..................... 433/225 |
| D249,705 | S | | 9/1978 | London |
| 4,257,411 | A | | 3/1981 | Cho |
| 4,338,054 | A | | 7/1982 | Dahl |
| 4,386,179 | A | | 5/1983 | Sterling |
| 4,535,768 | A | | 8/1985 | Hourahane et al. |
| 4,537,185 | A | * | 8/1985 | Stednitz ....................... 606/304 |
| 4,756,307 | A | | 7/1988 | Crowninshield |
| 4,903,692 | A | * | 2/1990 | Reese .......................... 606/99 |
| 4,922,897 | A | | 5/1990 | Sapega et al. |
| 4,932,972 | A | | 6/1990 | Dunn et al. |
| 4,950,270 | A | * | 8/1990 | Bowman et al. .............. 606/916 |
| 4,985,032 | A | | 1/1991 | Goble |
| 4,998,937 | A | | 3/1991 | Grimes |

(Continued)

FOREIGN PATENT DOCUMENTS

EP 1360949 11/2003

(Continued)

OTHER PUBLICATIONS

Allen et al., "Degradation and stabilization of styrene-ethylene-butadiene-styrene (SEBS) block copolymer", Polymer Degradation and Stability, V. 71, p. 113-122. (2001).

*Primary Examiner* — Eduardo C Robert
*Assistant Examiner* — Lynnsy Schneider
(74) *Attorney, Agent, or Firm* — Harness, Dickey

(57) ABSTRACT

A method for securing a soft tissue replacement in a bone tunnel includes forming a first and second tunnel in the bone. The second tunnel intersects the first tunnel and defines a first and second access passage. A first flexible member is passed through the tunnel and includes a first end extending out of the first passage, an intermediate portion supporting the soft tissue replacement and a second end extending out of the second passage. The first end of the first flexible member is fastened to an insertion member. A crosspin is positioned between the first passage and the insertion member. The second end of the first flexible member is advanced until a distal portion of the crosspin advances into the first access passage. The insertion member is impacted thereby pushing the crosspin into an engaged position with the bone.

10 Claims, 10 Drawing Sheets

U.S. PATENT DOCUMENTS

| | | | |
|---|---|---|---|
| 5,004,474 A | 4/1991 | Fronk et al. | |
| 5,019,078 A | 5/1991 | Perren et al. | |
| 5,026,374 A | 6/1991 | Dezza et al. | |
| 5,030,219 A | 7/1991 | Matsen, III et al. | |
| 5,041,129 A * | 8/1991 | Hayhurst et al. | 606/232 |
| 5,098,435 A | 3/1992 | Stednitz et al. | |
| 5,100,405 A | 3/1992 | McLaren | |
| 5,100,417 A * | 3/1992 | Cerier et al. | 606/139 |
| 5,108,396 A | 4/1992 | Lackey et al. | |
| 5,112,336 A | 5/1992 | Krevolin et al. | |
| 5,129,902 A | 7/1992 | Goble et al. | |
| 5,139,520 A * | 8/1992 | Rosenberg | 606/87 |
| 5,141,520 A * | 8/1992 | Goble et al. | 606/232 |
| 5,176,682 A * | 1/1993 | Chow | 606/232 |
| 5,192,322 A | 3/1993 | Koch et al. | |
| 5,201,744 A | 4/1993 | Jones | |
| 5,224,946 A * | 7/1993 | Hayhurst et al. | 606/232 |
| 5,234,434 A | 8/1993 | Goble et al. | |
| 5,234,444 A | 8/1993 | Christoudias | |
| 5,257,996 A | 11/1993 | McGuire | |
| 5,258,016 A * | 11/1993 | DiPoto et al. | 606/232 |
| 5,266,075 A | 11/1993 | Clark et al. | |
| 5,300,077 A | 4/1994 | Howell | |
| 5,350,380 A | 9/1994 | Goble et al. | |
| 5,354,298 A * | 10/1994 | Lee et al. | 606/139 |
| 5,354,300 A | 10/1994 | Goble et al. | |
| 5,356,413 A * | 10/1994 | Martins et al. | 606/75 |
| 5,370,646 A * | 12/1994 | Reese et al. | 606/324 |
| 5,370,662 A * | 12/1994 | Stone et al. | 606/232 |
| 5,391,029 A | 2/1995 | Fardell | |
| 5,393,302 A | 2/1995 | Clark et al. | |
| 5,397,356 A | 3/1995 | Goble et al. | |
| D357,534 S | 4/1995 | Hayes | |
| 5,423,823 A | 6/1995 | Schmieding | |
| 5,425,733 A | 6/1995 | Schmieding | |
| 5,431,651 A * | 7/1995 | Goble | 606/916 |
| 5,437,677 A | 8/1995 | Shearer et al. | |
| 5,454,365 A | 10/1995 | Bonutti | |
| 5,456,722 A | 10/1995 | McLeod et al. | |
| 5,480,403 A * | 1/1996 | Lee et al. | 606/232 |
| 5,507,812 A | 4/1996 | Moore | |
| 5,540,703 A | 7/1996 | Barker, Jr. et al. | |
| 5,545,180 A * | 8/1996 | Le et al. | 606/232 |
| 5,549,676 A | 8/1996 | Johnson | |
| 5,562,671 A | 10/1996 | Goble et al. | |
| 5,593,408 A | 1/1997 | Gayet et al. | |
| 5,601,562 A | 2/1997 | Wolf et al. | |
| 5,618,314 A * | 4/1997 | Harwin et al. | 606/232 |
| 5,632,748 A * | 5/1997 | Beck et al. | 606/89 |
| 5,643,273 A | 7/1997 | Clark | |
| 5,643,320 A * | 7/1997 | Lower et al. | 606/232 |
| 5,665,121 A | 9/1997 | Gie et al. | |
| 5,674,224 A | 10/1997 | Howell et al. | |
| 5,849,013 A | 12/1998 | Whittaker et al. | |
| 5,868,789 A * | 2/1999 | Huebner | 606/232 |
| 5,891,150 A * | 4/1999 | Chan | 606/96 |
| 5,895,425 A | 4/1999 | Grafton et al. | |
| 5,918,604 A | 7/1999 | Whelan | |
| 5,931,839 A | 8/1999 | Medoff | |
| 5,941,885 A * | 8/1999 | Jackson | 606/104 |
| 5,964,764 A | 10/1999 | West, Jr. et al. | |
| 5,980,558 A * | 11/1999 | Wiley | 606/232 |
| 5,984,966 A * | 11/1999 | Kiema et al. | 623/13.14 |
| 6,039,739 A | 3/2000 | Simon et al. | |
| 6,066,173 A | 5/2000 | McKernan et al. | |
| 6,068,648 A * | 5/2000 | Cole et al. | 606/232 |
| 6,110,211 A | 8/2000 | Weiss | |
| 6,113,604 A | 9/2000 | Whittaker et al. | |
| 6,132,433 A | 10/2000 | Whelan | |
| 6,146,406 A * | 11/2000 | Shluzas et al. | 606/232 |
| 6,187,742 B1 | 2/2001 | Wozney et al. | |
| 6,224,598 B1 * | 5/2001 | Jackson | 606/305 |
| 6,231,608 B1 | 5/2001 | Stone | |
| 6,231,611 B1 | 5/2001 | Mosseri et al. | |
| 6,267,766 B1 | 7/2001 | Burkhart | |
| 6,280,474 B1 * | 8/2001 | Cassidy et al. | 623/16.11 |
| 6,306,138 B1 | 10/2001 | Clark et al. | |
| 6,325,804 B1 | 12/2001 | Wenstrom, Jr. et al. | |
| 6,342,056 B1 | 1/2002 | Mac-Thiong et al. | |
| 6,371,124 B1 | 4/2002 | Whelan | |
| 6,375,684 B1 | 4/2002 | Kriek et al. | |
| 6,379,384 B1 | 4/2002 | McKernan et al. | |
| 6,383,199 B2 | 5/2002 | Carter et al. | |
| 6,436,099 B1 * | 8/2002 | Drewry et al. | 606/61 |
| 6,440,373 B1 * | 8/2002 | Gomes et al. | 422/102 |
| 6,454,768 B1 * | 9/2002 | Jackson | 606/61 |
| 6,494,913 B1 | 12/2002 | Huebner | |
| 6,497,726 B1 | 12/2002 | Carter et al. | |
| 6,499,486 B1 * | 12/2002 | Chervitz et al. | 128/898 |
| 6,511,958 B1 | 1/2003 | Atkinson et al. | |
| 6,514,514 B1 | 2/2003 | Atkinson et al. | |
| 6,517,546 B2 | 2/2003 | Whittaker et al. | |
| 6,517,579 B1 | 2/2003 | Paulos et al. | |
| 6,524,328 B2 * | 2/2003 | Levinson | 606/232 |
| 6,537,319 B2 | 3/2003 | Whelan | |
| 6,540,783 B1 | 4/2003 | Whittaker et al. | |
| 6,562,043 B1 * | 5/2003 | Chan | 606/65 |
| 6,562,044 B1 | 5/2003 | Cooper | |
| 6,562,071 B2 | 5/2003 | Jarvinen et al. | |
| 6,589,281 B2 | 7/2003 | Hyde, Jr. | |
| 6,610,064 B1 | 8/2003 | Goble et al. | |
| 6,623,524 B2 * | 9/2003 | Schmieding | 623/13.14 |
| 6,673,115 B2 | 1/2004 | Resch et al. | |
| 6,712,823 B2 | 3/2004 | Grusin et al. | |
| 6,730,089 B2 * | 5/2004 | Jackson | 606/270 |
| 6,733,529 B2 | 5/2004 | Whelan | |
| 6,752,830 B1 * | 6/2004 | Goble et al. | 623/13.14 |
| 6,755,840 B2 | 6/2004 | Boucher et al. | 606/96 |
| 6,780,188 B2 | 8/2004 | Clark et al. | |
| 6,878,166 B2 * | 4/2005 | Clark et al. | 623/13.12 |
| 6,887,271 B2 | 5/2005 | Justin et al. | |
| 7,022,124 B2 * | 4/2006 | Takei et al. | 606/99 |
| 7,033,364 B1 | 4/2006 | Walters et al. | |
| 7,229,448 B2 * | 6/2007 | Goble et al. | 606/98 |
| 7,285,121 B2 * | 10/2007 | Braun et al. | 606/73 |
| 7,309,337 B2 * | 12/2007 | Colleran et al. | 606/232 |
| 7,341,592 B1 | 3/2008 | Walters et al. | |
| 7,458,975 B2 * | 12/2008 | May et al. | 606/53 |
| 7,588,595 B2 * | 9/2009 | Miller et al. | 606/323 |
| 7,601,165 B2 | 10/2009 | Stone | |
| 7,645,293 B2 * | 1/2010 | Martinek et al. | 606/232 |
| 2001/0039455 A1 | 11/2001 | Simon et al. | |
| 2001/0044627 A1 * | 11/2001 | Justin | 606/72 |
| 2001/0047210 A1 | 11/2001 | Wolf | |
| 2001/0053934 A1 | 12/2001 | Schmieding | |
| 2002/0019635 A1 | 2/2002 | Wenstrom et al. | |
| 2002/0058941 A1 | 5/2002 | Clark et al. | |
| 2002/0077631 A1 | 6/2002 | Lubbers et al. | |
| 2002/0087160 A1 * | 7/2002 | Clark et al. | 606/72 |
| 2002/0099381 A1 | 7/2002 | Maroney | |
| 2002/0111689 A1 | 8/2002 | Hyde | |
| 2002/0111690 A1 | 8/2002 | Hyde | |
| 2002/0133153 A1 | 9/2002 | Hyde | |
| 2002/0138148 A1 | 9/2002 | Hyde | |
| 2002/0138149 A1 | 9/2002 | Hyde | |
| 2003/0028194 A1 * | 2/2003 | St. Pierre et al. | 606/73 |
| 2003/0032961 A1 | 2/2003 | Pelo et al. | |
| 2003/0065332 A1 | 4/2003 | TenHuisen et al. | |
| 2003/0097179 A1 | 5/2003 | Carter et al. | |
| 2003/0105524 A1 | 6/2003 | Paulos et al. | |
| 2003/0163202 A1 | 8/2003 | Lakin | |
| 2004/0087953 A1 * | 5/2004 | Singhatat et al. | 606/72 |
| 2004/0092936 A1 | 5/2004 | Miller et al. | |
| 2005/0038426 A1 | 2/2005 | Chan | |
| 2005/0137704 A1 | 6/2005 | Steenlage | |
| 2005/0149187 A1 | 7/2005 | Clark et al. | |
| 2005/0177165 A1 * | 8/2005 | Zang et al. | 606/73 |
| 2005/0197662 A1 | 9/2005 | Clark et al. | |
| 2005/0203622 A1 | 9/2005 | Steiner et al. | |
| 2005/0273003 A1 | 12/2005 | Walters et al. | |

| | | | |
|---|---|---|---|
| 2006/0229722 A1 | 10/2006 | Bianchi et al. | |
| 2007/0168043 A1* | 7/2007 | Ferree | 623/17.16 |
| 2008/0027443 A1 | 1/2008 | Lambert | |
| 2008/0228271 A1 | 9/2008 | Stone et al. | |

FOREIGN PATENT DOCUMENTS

FR 2684543 6/1993

* cited by examiner

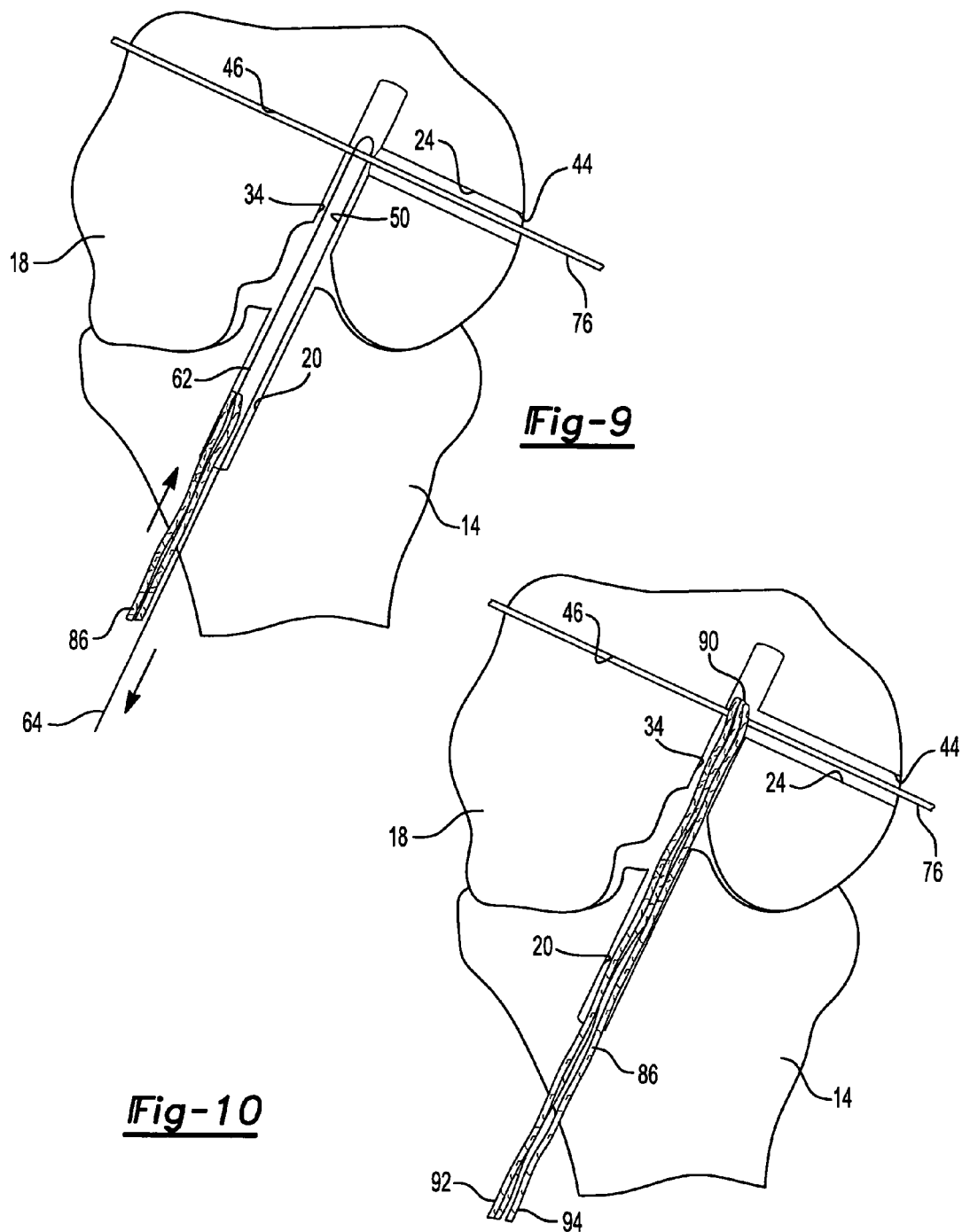

CROSSPIN AND METHOD FOR INSERTING THE SAME DURING SOFT LIGAMENT REPAIR

FIELD OF THE INVENTION

The present invention relates to endoscopic soft tissue replacement fixation. More particularly, the present invention relates to an apparatus and a method to reconstruct an anterior cruciate ligament with soft tissue replacements within a femoral tunnel.

BACKGROUND OF THE INVENTION

The knee joint is frequently the object of injury and is often repaired using arthroscopic surgical procedures. An example of such arthroscopic surgery is the replacement of anterior cruciate ligaments of the knee. The tearing of these ligaments is common in sports activities such as football or skiing.

In some prior art procedures, it has been difficult to insert and fasten a soft tissue replacement in a blind bore or tunnel. Attempts have been made to thread the soft tissue replacement through the tunnel and over an anchor, but with some difficulty. Thus far, there is need for improvement in the prior art to develop a quick and efficient method to implant a soft tissue replacement over an implanted anchoring system.

Other techniques attempt to use biological fixation to augment or replace mechanical fixation. While increasing fixation strength, these techniques require time to fully realize their fixation potential. Additionally, the techniques may take additional surgical time and resources that a purely mechanical fixation technique may not require.

SUMMARY OF THE INVENTION

A method for securing a soft tissue replacement in a bone tunnel includes forming a first tunnel in the bone. A second tunnel is formed through the bone and defines a first and second access passage on opposite ends of the second tunnel. The second tunnel intersects the first tunnel. A first flexible member is passed through the tunnel and includes a first end extending out of the first passage, an intermediate portion supporting the soft tissue replacement and a second end extending out of the second passage.

The first end of the first flexible member is fastened to an insertion member. A crosspin is positioned between the first passage and the insertion member. The second end of the first flexible member is advanced until a distal portion of the crosspin advances into the first access passage. The insertion member is impacted thereby pushing the crosspin into an engaged position with the bone.

A system for securing a soft tissue replacement in a bone tunnel includes a crosspin adapted to be inserted into a femoral tunnel and support the soft tissue replacement. An insertion member includes a distal end adapted to matingly engage a proximal end of the crosspin. The insertion member is adapted to push the crosspin into an engaged position whereby the soft tissue replacement is in a secure relationship with the bone.

According to other features, a first flexible member is adapted to be pulled through the femoral tunnel. The first flexible member is adapted to be coupled to the insertion member and pull the insertion member toward the bone thereby locating the crosspin into an engaged position with the femoral tunnel. The system further comprises an impacting tool for imposing a force onto the insertion member in a direction toward the bone.

A crosspin for use in soft tissue replacement surgery includes a distal tip portion, an intermediate portion transitioning from the distal portion at a ramp portion, and a longitudinal slot defined by the intermediate portion. The longitudinal slot extends from a first outer longitudinal surface to a terminal longitudinal surface. The terminal longitudinal surface defines a terminal axis, wherein the terminal axis is offset from an axis defining a centerline of a longitudinal axis of the crosspin.

A crosspin for use in soft tissue replacement surgery includes a distal portion, an intermediate portion and a proximal portion having a proximal end. The proximal end includes fin portions formed thereon and defines a first outer dimension. The fin portions are adapted to progressively deflect inwardly upon impacting the proximal end in a direction toward the distal portion during insertion of the crosspin into a bone tunnel. The fin portions provide an outward retention force onto a surface of the bone tunnel in an installed position.

A crosspin for use in soft tissue replacement surgery includes a distal portion, an intermediate portion, a proximal portion and a breakaway portion. The breakaway portion extends from the proximal portion and is adapted to be disconnected from the proximal portion upon locating the crosspin at a desired depth in the bone tunnel.

According to other features, a driver is provided and is adapted to cooperate with the breakaway portion and impose a force onto the breakaway portion causing the breakaway portion to disconnect from the proximal portion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 9 is an anterior view of the soft tissue replacement being passed over the pin;

FIG. 10 is an anterior view of the soft tissue replacement looped over and supported by the pin;

DETAILED DESCRIPTION OF THE PREFERRED EMBODIMENTS

Figure 1:
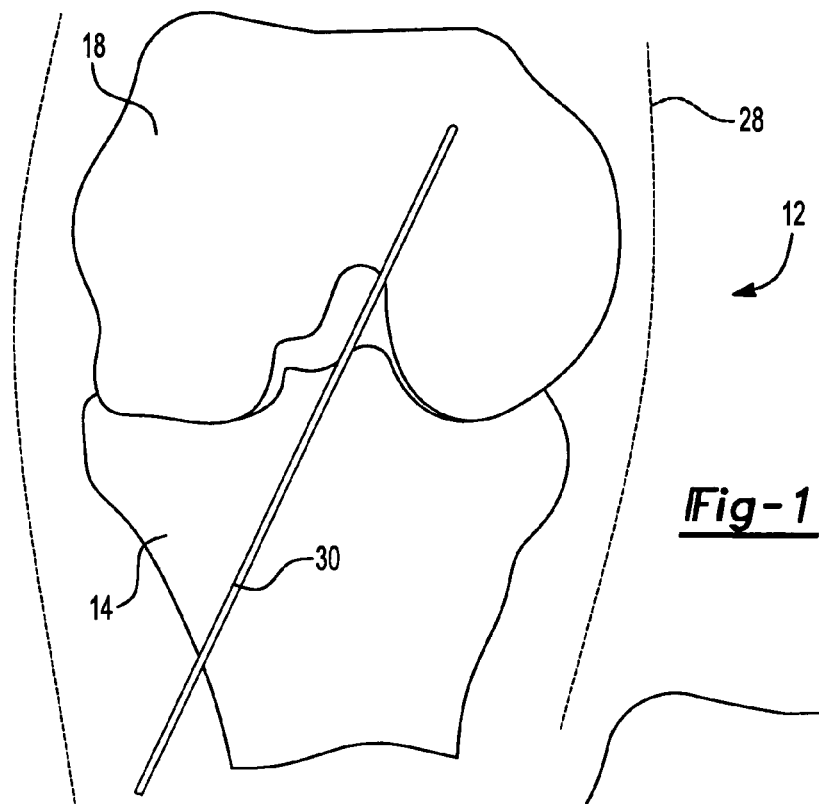
FIG. 1 is an anterior view of a guide wire forming a preliminary tunnel through a portion of the tibia and femur.

The following description of the embodiment(s) is merely exemplary in nature and is in no way intended to limit the invention, its application, or uses. Moreover, while the present teachings are discussed in detail below with regard to ACL reconstruction, those skilled in the art will recognize the other types of soft tissue fixation may employ the present teachings.

Referring to the drawings, a crosspin 10 (FIG. 11) and a method for implanting the crosspin 10 during ACL reconstruction is shown. With particular reference to FIGS. 1-4, a knee 12 generally includes at least a tibia 14 and a femur 18 surrounded by soft tissue 28. The knee 12 is initially prepared by forming a tibial tunnel 20 and a femoral tunnel 24 which are substantially in line with one another such that a straight and solid object could engage both the tibial tunnel 20 and the femoral tunnel 24 without a substantial amount of stress when the knee 10 is placed in flexion between about 30 and about 110 degrees. It is understood that incisions must first be made in the soft tissue 28 (FIG. 1) surrounding the tibia 14 such that a tool may engage the tibia 14 and the femur 18 to form the tibial tunnel 20 and the femoral tunnel 24.

Figure 2:
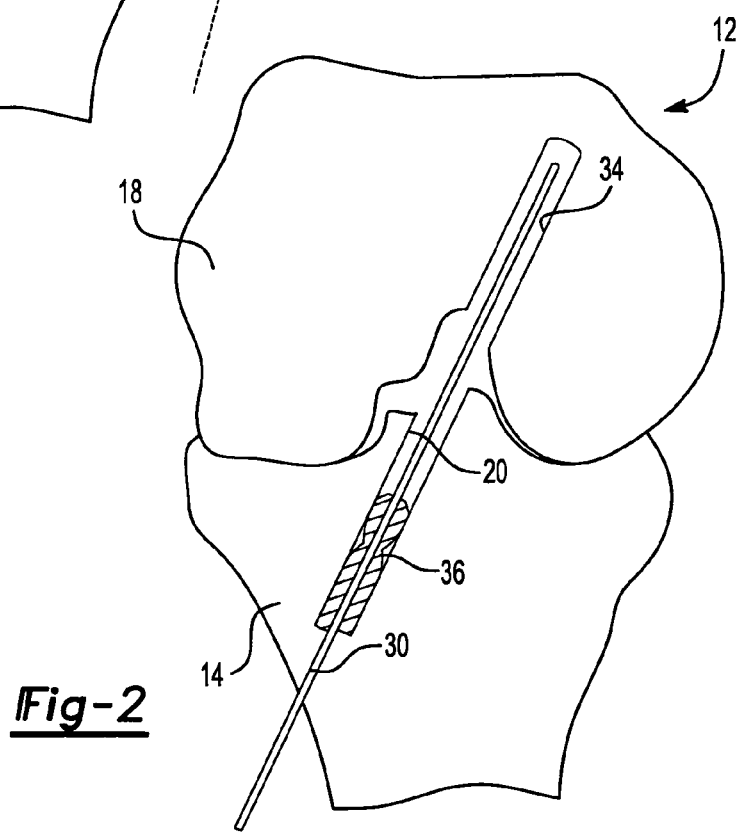
FIG. 2 is an anterior view of a cannulated drill forming a tunnel in the tibia and femur.

With specific reference to FIGS. 1 and 2, a device such as a guide wire or K-wire 30 is used to produce a preliminary tunnel passing through a portion of the tibia 14 and a portion of the femur 18 when the knee is flexed. A blind femoral tunnel 34 is then formed in the femur 18 with a cannulated drill/reamer 36 guided along the guide wire 30 to enlarge the tunnel 20. The blind femoral tunnel 34 terminates below the surface of the femur 18 and includes an entrance but no discernable exit. It is appreciated that the femoral tunnel 34 may alternatively form an exit through the femur 18.

Figure 3:
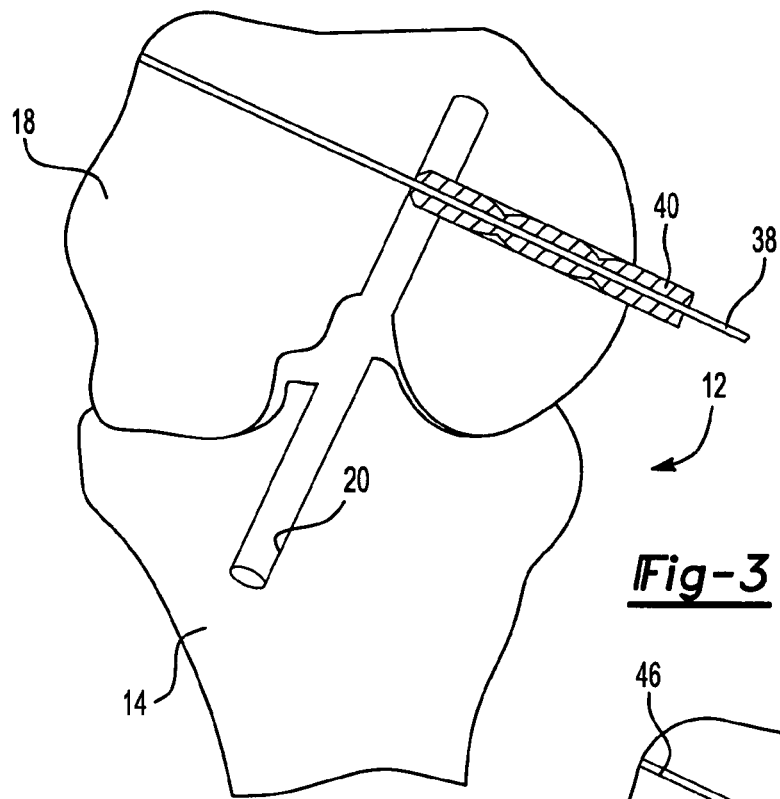
FIG. 3 is an anterior view of a guide wire and cannulated drill forming a femoral tunnel.
Figure 4:
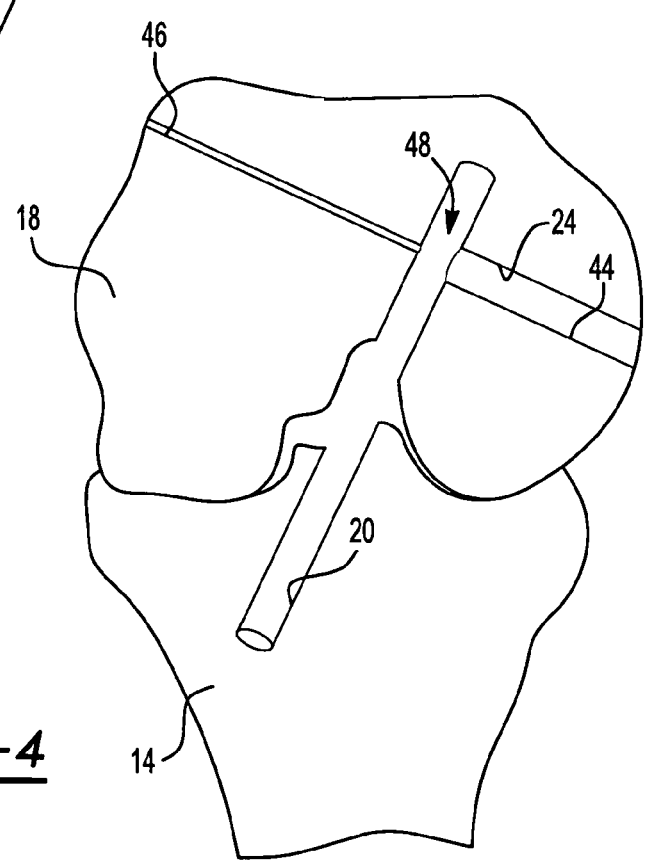
FIG. 4 is an anterior view of the respective tibial and femoral tunnels.

Turning to FIGS. 3 and 4, the femoral tunnel 24 is formed by forming a preliminary tunnel with a guide wire 38. Next, a cannulated drill/reamer 40 is guided along the guide wire 38 to form the femoral tunnel 24 defining a first and second access passage 44 and 46, respectively. The respective femoral tunnels 20 and 24 intersect at an intersection area 48 (FIG. 4). While the femoral tunnel 24 is shown having a consistent outer diameter from the first and second access passages 44 and 46, it is appreciated that the femoral tunnel 24 may alternatively be reamed to a predetermined location between the intersection area 48 and the second access passage 46 or a distance sufficient to accept the crosspin 10 into a desired position.

Those skilled in the art will appreciate that any suitable tool may produce the respective tunnels such as a pneumatic or electric drill or reamer. Furthermore, the diameter of the tibial tunnel 20 and the femoral tunnel 24 depends upon the size of the soft tissue replacement (described further herein) to be implanted into the patient. The larger the replacement needed, the larger the diameter of the tibial tunnel 20 and the femoral tunnel 24. The tibial tunnel 20 and the femoral tunnel 24 may be of any required diameter, but are generally between about 5 and about 18 millimeters. It is appreciated, however, should a larger diameter replacement be necessary, a larger diameter may be produced in the tibia 14 and the femur 18 to receive the implant. Likewise, smaller tunnels may be formed if a smaller implant is necessary.

With further reference to FIGS. 5-8, the method of implanting the crosspin 10 will be further described. Once the respective tibial and femoral tunnels 20 and 24 are formed, a flexible member 50 is introduced into the tibial tunnel. The flexible member 50 may be any generally known flexible member suitable for the purpose such as a mono- or poly-filament suture, a flexible wire, or cord made of any suitable material. The flexible member 50 is positioned at the intersection area 48 with an insertion instrument or fork 54. Specifically, the fork 54 includes a shaft portion 56 and a pair of cannulated finger portions 58 and 60. The flexible member 50 is across the respective finger portions 58 and 60 of the cannulated fork 54 such that opposite ends 62 and 64 of the flexible member 50 extend adjacent to proximal end 68 of the fork 54. A loop portion 70 is formed at an intermediate portion 72 of the flexible member 50 and extends between the respective fingers 58 and 60.

Figure 5:
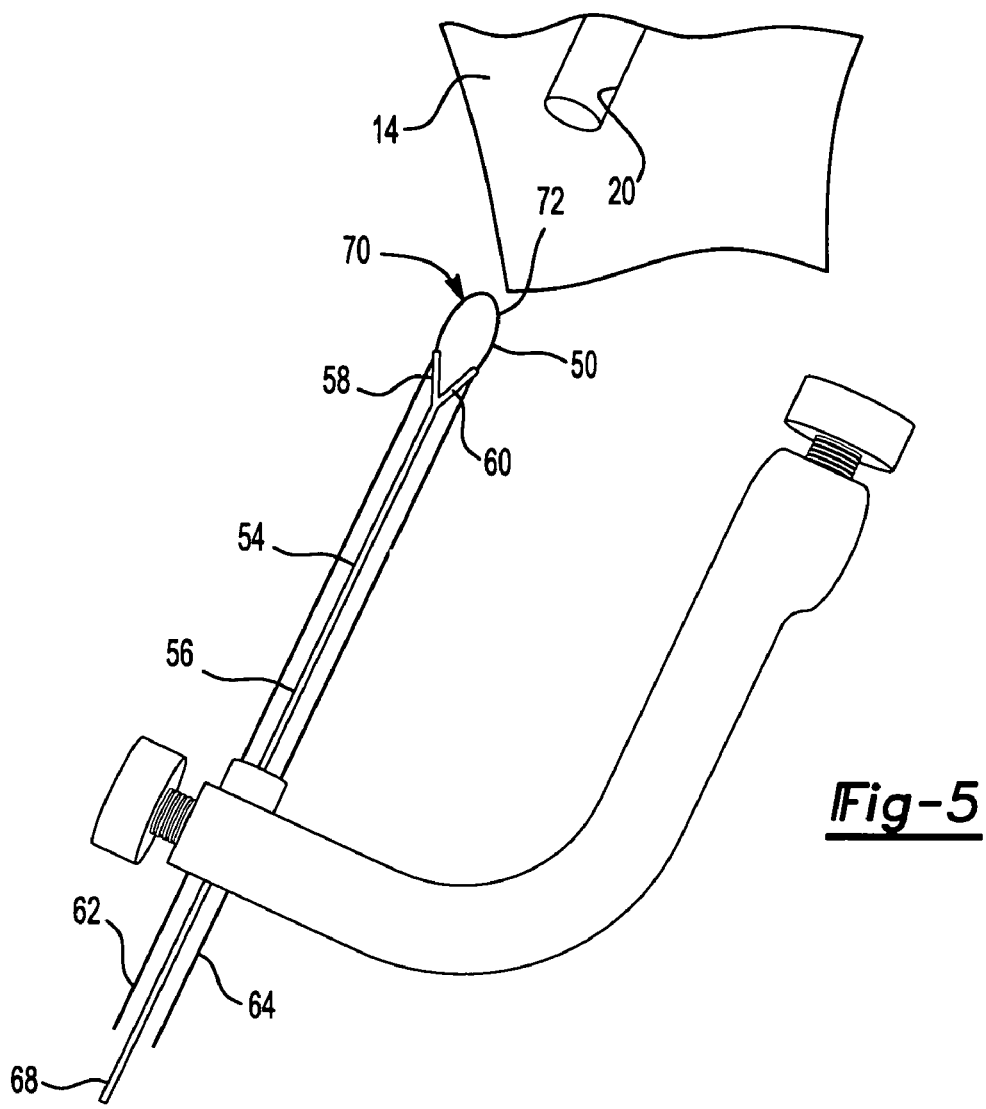
FIG. 5 is an anterior view of an insertion instrument cooperating with a flexible member.
Figure 5A:
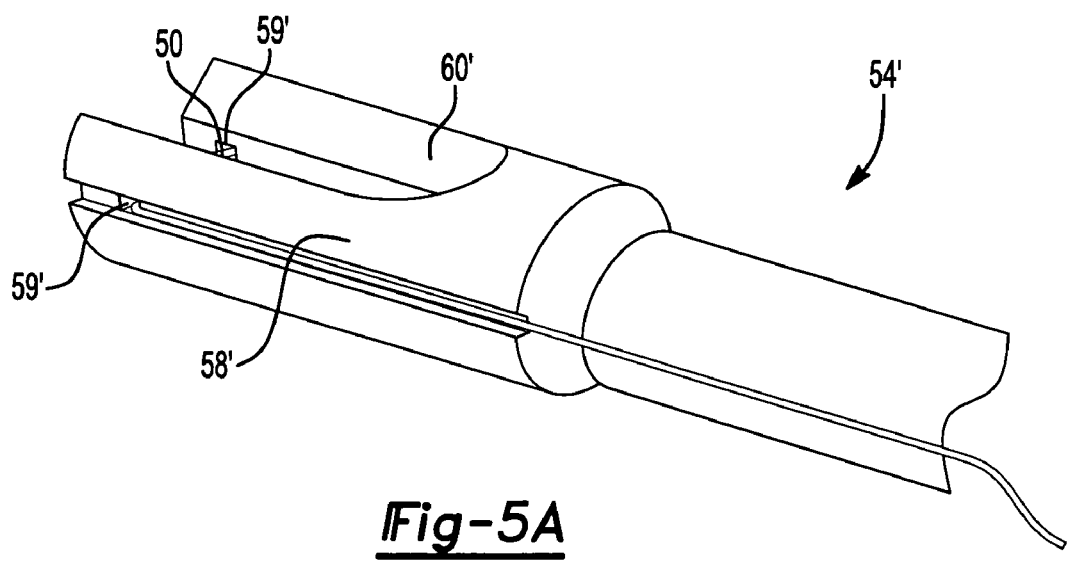
FIG. 5A is a perspective view of an insertion instrument according to additional features.
Figure 5B:
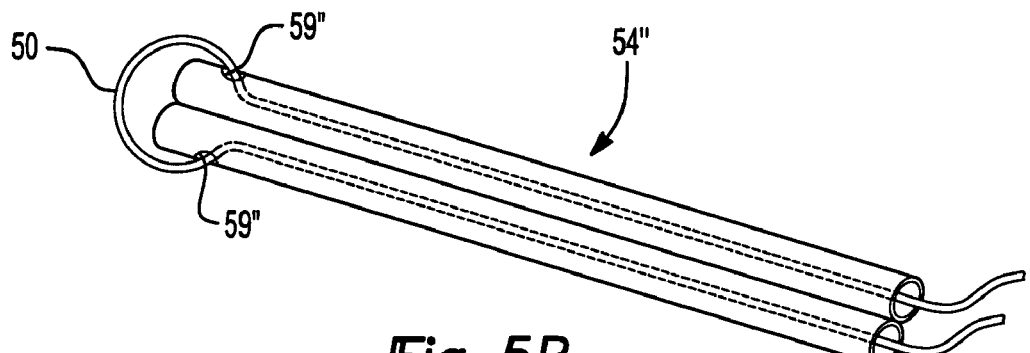
FIG. 5B is a perspective view of an insertion instrument according to additional features.
Figure 5C:
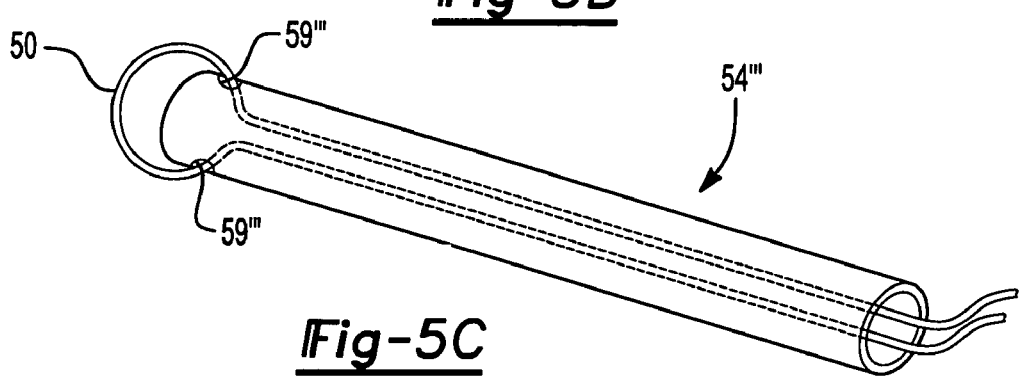
FIG. 5C is a perspective view of an insertion instrument according to additional features.
Figure 6:
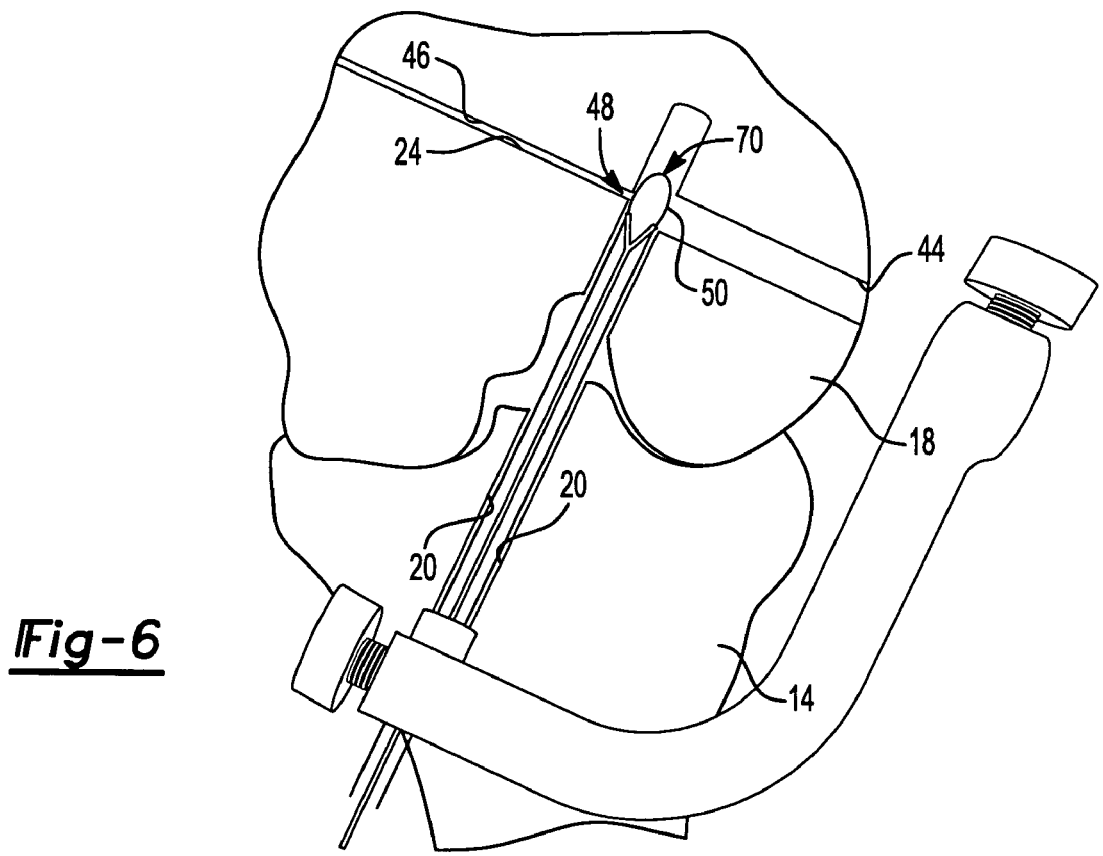
FIG. 6 is an anterior view of the insertion instrument locating a looped portion of the flexible member into the femoral tunnel.
Figure 7:
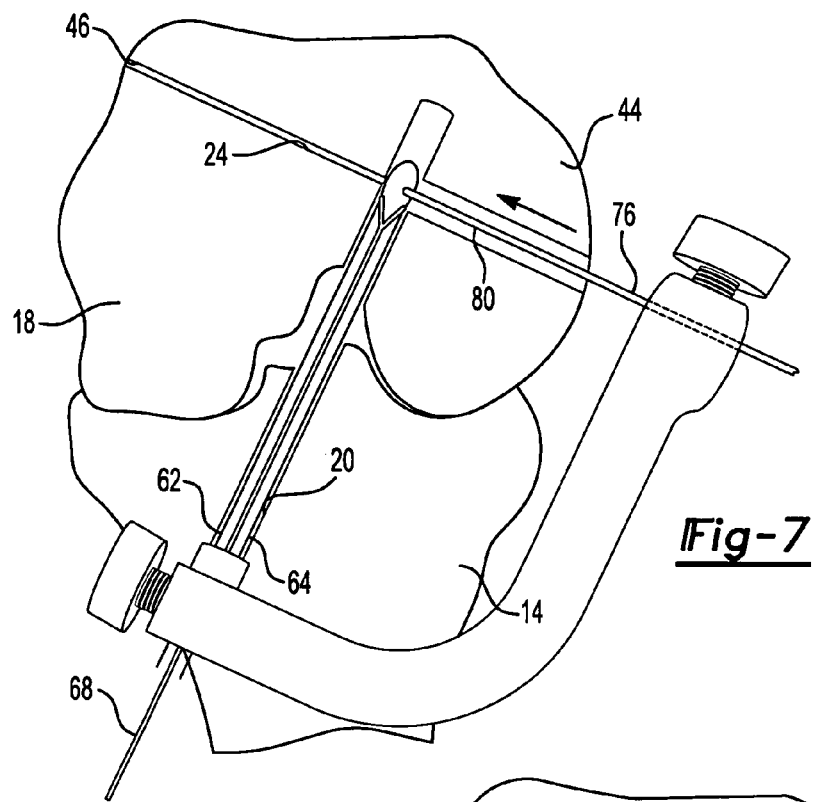
FIG. 7 is an anterior view of a pin inserted into the femoral tunnel to pass through the loop in the flexible member.

With reference to FIG. 5A, an insertion instrument 54' according to additional features is shown. The insertion instrument 54' includes a pair of fingers 58' and 60'. A transverse passage 59' accommodates a flexible member 50 therethrough. With reference to FIG. 5B, an insertion instrument 54" according to additional features is shown. The insertion instrument 54" includes a dual tube configuration having a passage 59" defined at a distal end for accommodating a flexible member 50. With reference to FIG. 5C, an insertion instrument 54''' according to additional features is shown. The insertion instrument 54''' includes a single tube configuration having a passage 59''' defined at a distal end for accommodating a flexible member 50. Those skilled in the art will appreciate that an intermediate portion 72 of the flexible member 50 may be inserted at the intersection area 48 by other methods and with other devices.

Figure 8:
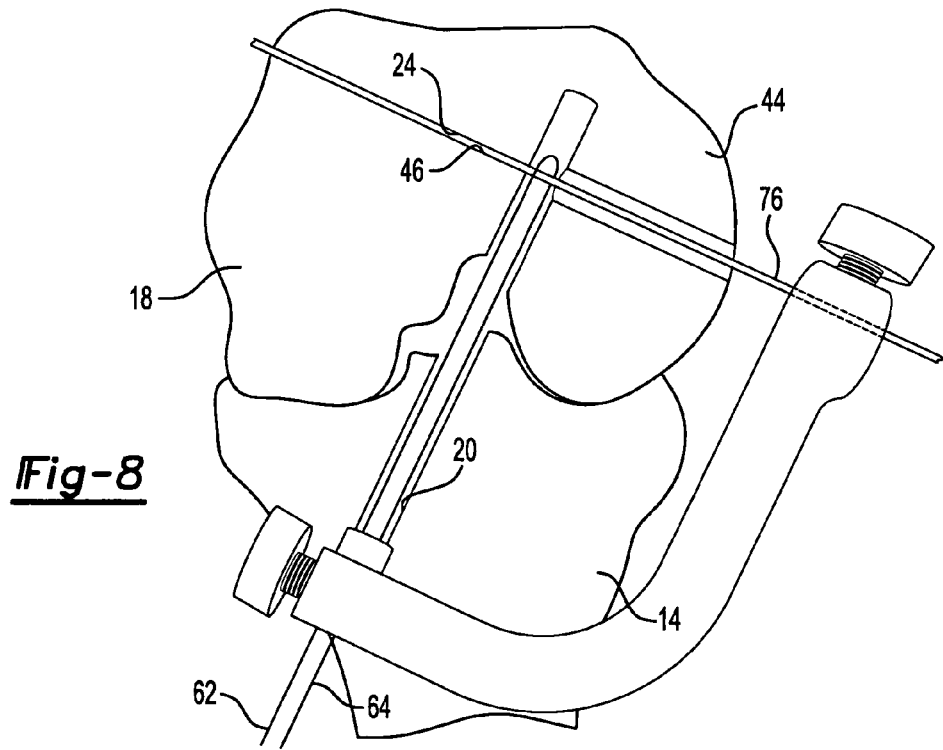
FIG. 8 is an anterior view of FIG. 7 shown with the insertion instrument removed and the flexible member looped over and supported by the pin.

Once the looped portion 70 is presented at the intersection area 48, a guide wire or pin 76 is inserted into the femoral tunnel 24 at the first access passage 44. The pin 76 passes through the loop portion 70 of the flexible member 50 and is passed until a distal end 80 (FIG. 7) extends through the second access passage 46 (FIG. 8). Next, the insertion instrument 54 may be removed from the tibial tunnel 20. Movement of the insertion instrument 54 downward (as viewed in FIG. 7) allows the flexible member 50, supported by the pin 76, to maintain the intermediate portion 72 at a location passing over and supported by the pin 76. The opposite ends 62 and 64 of the flexible member 50 extend out of the tibial tunnel 20. It is appreciated that while the pin 76 is described herein as a distinct component from the drill bit 38 used to form the femoral tunnel 24, the drill bit 38 may likewise be employed to support the flexible member 50.

With particular reference to FIGS. 9 and 10 the positioning of a soft tissue replacement 86 will be described. The soft tissue replacement 86 is affixed to the first end 62 of the flexible member 50. The first end 62 of the flexible member 50 will hereinafter be referred to as the trailing end and the second end 64 of the flexible member 50 will hereinafter be referred to as the leading end for illustrative purposes. It is appreciated that the second end 64 of the flexible member 50 may alternatively be affixed to the soft tissue replacement 86 and therefore identified as the trailing end.

The soft tissue replacement 86 may be any suitable replacement such as a hamstring portion, an allograft tissue replacement, a xenograft tissue replacement or an artificial soft tissue replacement which may be produced from materials such as polymers or metal. After the soft tissue replacement 86 has been affixed to the trailing end 62, the leading end 64 of the flexible member 50 is pulled thereby drawing the soft tissue replacement 86 first through the tibial tunnel 20 and then through the femoral tunnel 24 over the pin 76 and back down the blind tunnel 34 and out through the tibial tunnel 20. This action produces a loop 90 of the soft tissue replacement 86 over the pin 76 inside of the femoral tunnel 24. After being looped over the pin 76, two free ends 92 and 94 of the soft tissue replacement 86 extend from the tibial tunnel 20 adjacent to the tibia 14 (FIG. 10).

Figure 11:
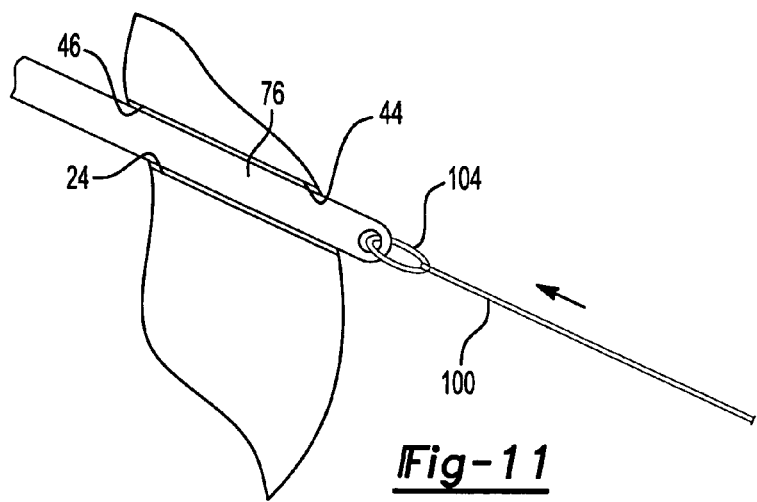
FIG. 11 is an anterior view of a flexible member being drawn through the femoral tunnel by the pin.
Figure 12:
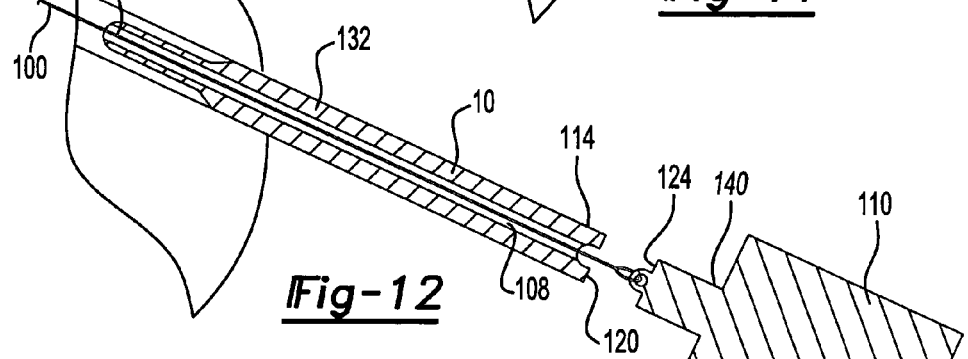
FIG. 12 is a sectional view of a crosspin and an insertion member used to push a crosspin into a desired location in the femoral tunnel.
Figure 13:
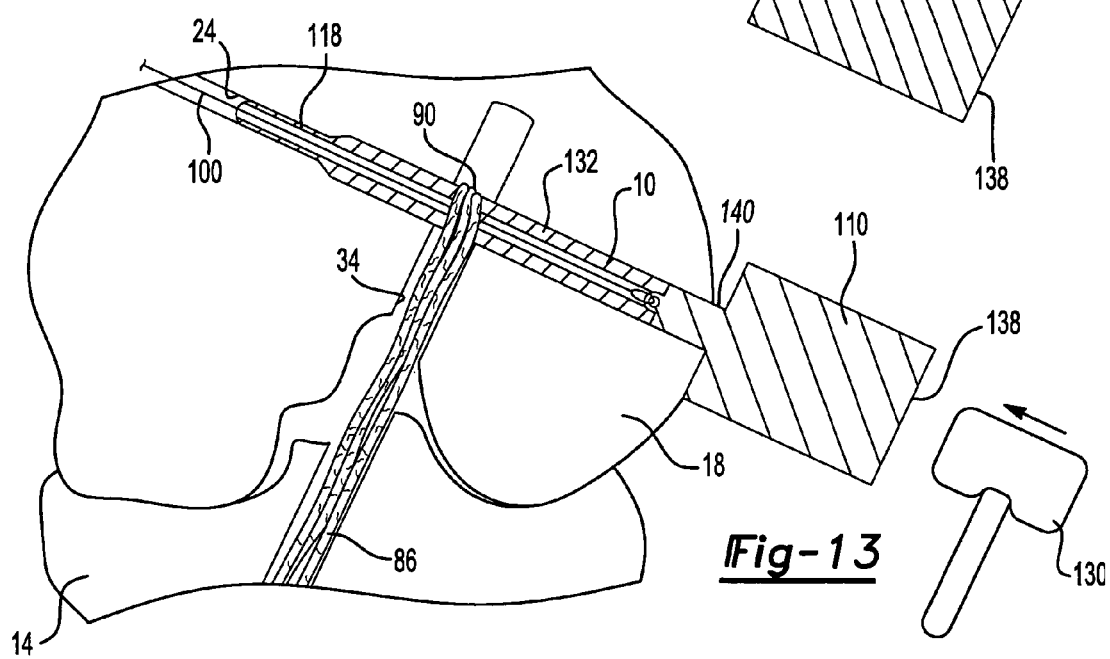
FIG. 13 is a sectional view of the crosspin shown being driven into the desired area with an impacting instrument to support the soft tissue replacement.

Turning now to FIGS. 11-13, once the soft tissue replacement 86 has been looped over the pin 76, the crosspin 10 is located into the femoral tunnel 24. First, a second flexible member 100 is drawn through the femoral tunnel 24 and under the soft tissue replacement 86. The second flexible member 100 is coupled to an eyelet 104 on the pin 76 and pulled through the tunnel 24 from the first access passage 44 and out the second access passage 42. It is appreciated that if the drill bit 38 was utilized to support the soft tissue replacement 86, an eyelet incorporated on a proximal end of the drill bit 38 may utilized to couple the second flexible member 100 thereat, and thereafter, draw the flexible member 100 through the tunnel 24.

Once the flexible member 100 extends out of the first access passage 44, it is passed through a cannulated portion 108 formed through the crosspin 10. Next, the flexible member 100 is coupled to an insertion member 110 proximate to a proximal end 114 of the crosspin 10. A distal end 118 of the crosspin 10 is then aligned at the first access passage 44 and the flexible member 100 is subsequently pulled from the second access passage 46 in a direction leftward as viewed from FIG. 12. This action allows the distal end 118 of the crosspin 10 to ingress into the tunnel 24 while locating the insertion member 110 into a nested, engaged position with the proximal end 114 of the crosspin 10 (FIG. 13).

The proximal end 114 of the crosspin 10 generally defines a square cross section. An intermediate portion 132 generally defines a circular cross section for mating with the wall of the femoral tunnel 24. The distal end 118 defines a circular stepped down extension from the intermediate portion 132. It is appreciated that the proximal end 114 and a proximal surface 120 of the crosspin 10 are configured to facilitate a mating engagement with an engagement end 124 of the insertion member 110.

With reference to FIG. 13, an impacting instrument 130 is used to impact an impacting surface 138 of the insertion member 110 in a direction toward the crosspin 10. Subsequent impacting causes the crosspin 10 to be pushed into the tunnel 24 until a desired location is achieved. During translation of the crosspin 10 from the first access passage 44 toward the second access passage 46, the soft tissue replacement 86 transitions from a looped relationship at the outer diameter of the distal portion 118 of the crosspin 10 to a looped relationship at the intermediate portion 132 of the crosspin 10. The insertion member 110 includes a neck portion 140 adapted to be received a predetermined distance into the femoral tunnel 24 at the first access passage 44. The insertion member 110 is subsequently disconnected from the flexible member 100. The crosspin 10 is comprised of a bioabsorbable material or any suitable biocompatible material.

Figure 14:
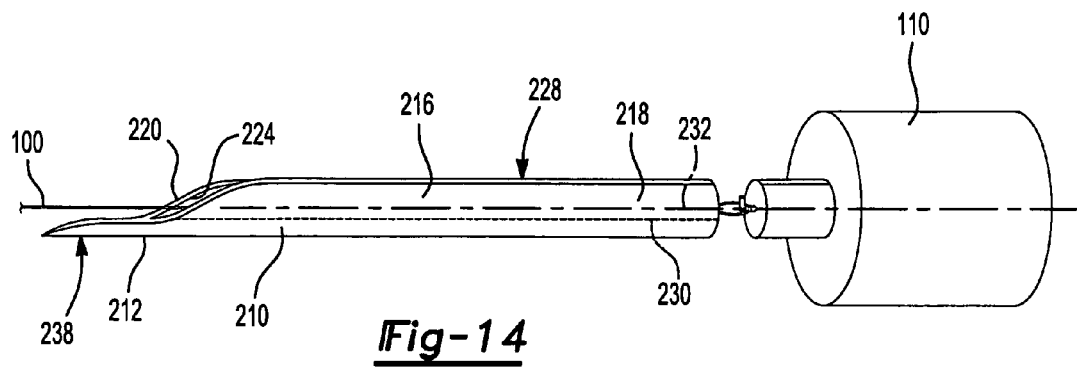
FIG. 14 is a perspective view of a crosspin according to additional features.
Figure 15:
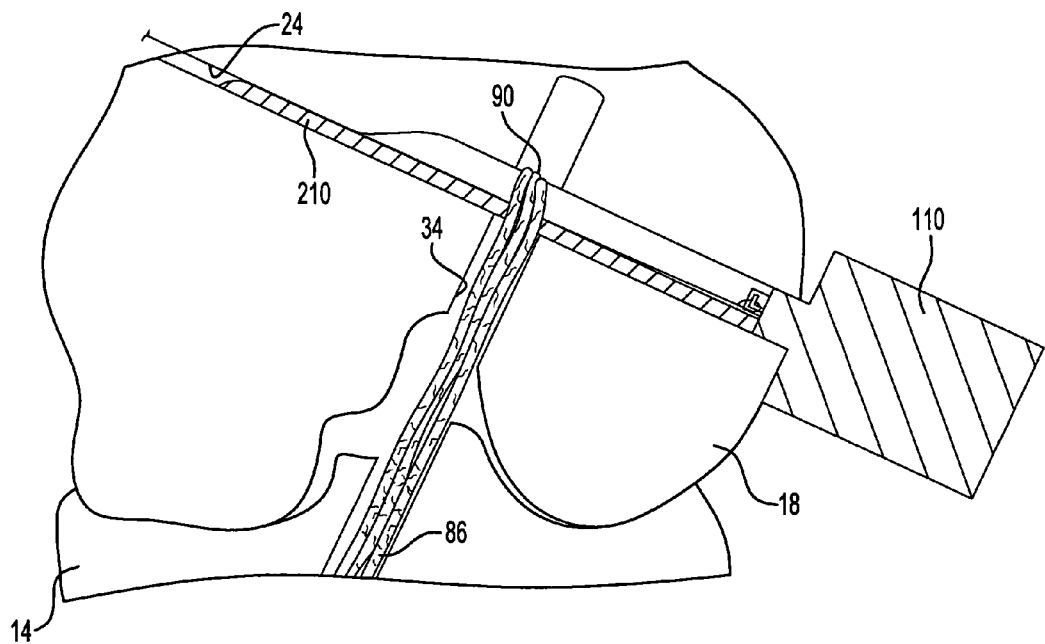
FIG. 15 is a partial sectional view of the crosspin of FIG. 14 shown driven into a desired location in the femoral tunnel.

With reference to FIGS. 14 and 15 a crosspin 210 according to other features is shown. The crosspin 210 includes a distal tip portion 212, an intermediate portion 216 and a proximal portion 218. A ramped transition portion 220 leads from the distal tip portion 212 to the intermediate portion 216. The ramped transition portion 220, intermediate portion 216 and the proximal portion 218 define a groove or longitudinal slot 224. The slot 224 is adapted to accept the flexible member 100 therethrough. The slot 224 is arranged from a first longitudinal surface 228 of the crosspin 210 to a terminal location 230 beyond a centerline 232 of the crosspin. In this way, the slot 224 of the crosspin 210 is offset from the centerline 232.

The distal tip portion 212 of the crosspin 210 extends from a second longitudinal surface 238 to the ramped portion 220 at the terminal location 230 of the slot 224. In this regard, the distal tip portion 212 presents a low profile approach to negotiate under the looped portion 90 of the soft tissue replacement 86. As the crosspin 210 is pushed into the tunnel 24 with the insertion member 110 according to the teachings above, the soft tissue replacement 86 is initially passed under by the distal tip portion 212, urged up the ramped portion 220 and finally communicated along the first longitudinal surface 228 until the desired location is achieved (FIG. 15).

Figure 16:
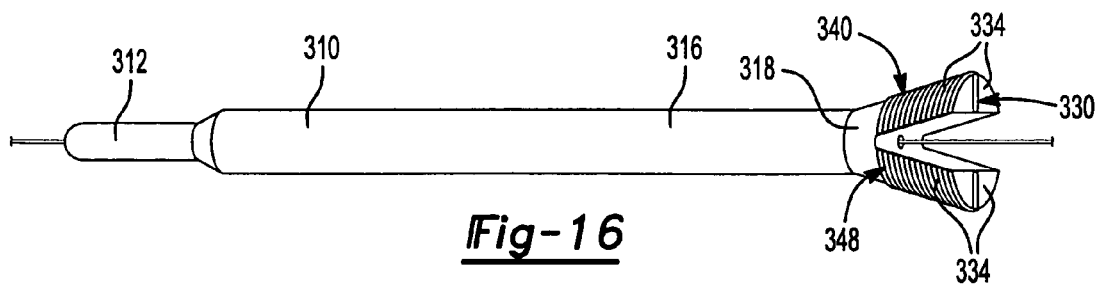
FIG. 16 is a perspective view of a crosspin according to additional features.
Figure 17:
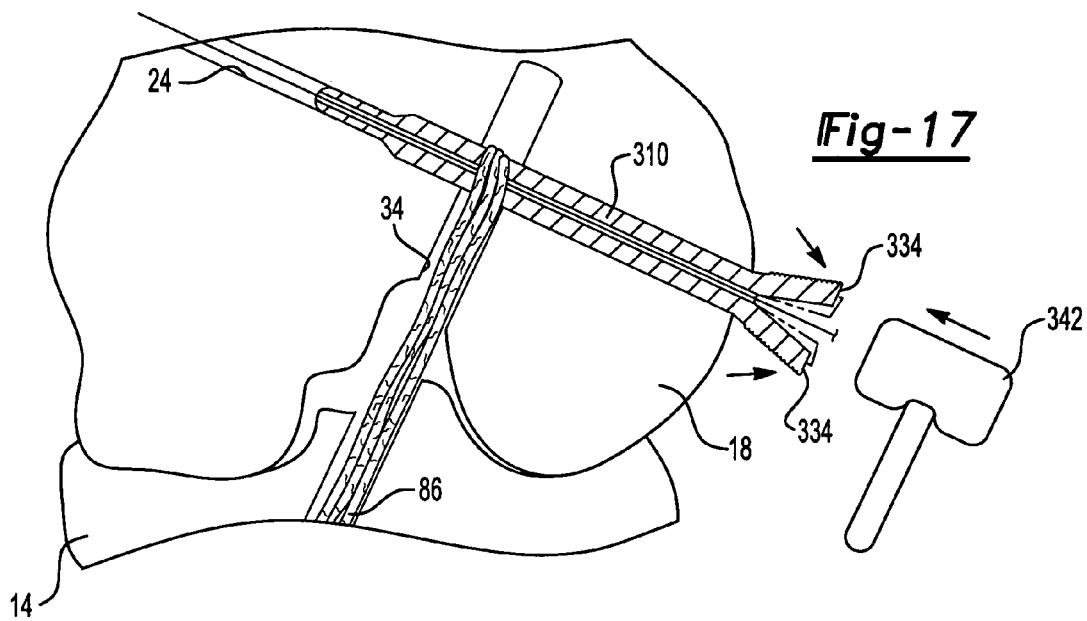
FIG. 17 is a sectional view of the crosspin of FIG. 16 shown being driven into the femoral tunnel with an impacting instrument.
Figure 18:
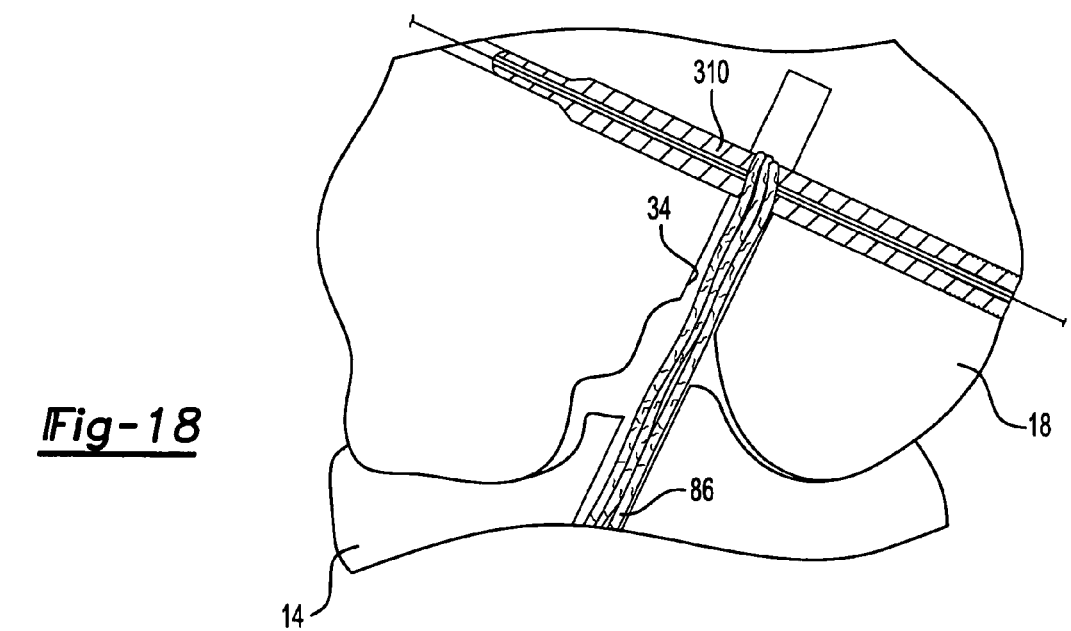
FIG. 18 is a sectional view of the crosspin of FIG. 17 shown inserted into a desired location in the femoral tunnel.

Turning now to FIGS. 16-18 a crosspin 310 according to other features will be described. The crosspin 310 generally includes a distal tip portion 312, an intermediate portion 316 and a proximal portion 318 having a proximal end 330. The proximal portion 318 includes a plurality of fin portions 334 formed thereon defining an outer dimension 340. The fin portions 334 are adapted to progressively deflect inwardly (FIG. 17) as the crosspin 310 ingresses into the femoral tunnel 24 upon impacting the proximal end 330 with an impacting tool 342. As the fin portions 334 ingress into the femoral tunnel, they provide a radial outward force into the wall of the femoral tunnel 24 thereby improving retention of the crosspin 10 in the femoral tunnel 24.

The impacting tool 342, such as a mallet, is adapted to impact the proximal end in a direction toward the distal portion 312 during insertion of the crosspin 310 into the femoral tunnel 24 to a desired location (FIG. 18). The fin portions 334 are tapered outwardly from the intermediate portion 316 to the proximal end 330. The fin portions 334 include arcuate outer surfaces 348 for cooperating with the outer wall of the femoral tunnel 24. In this way, the outer dimension 340 of the fins 334 define a conical surface. The outer surfaces 348 are threaded for facilitating removal of the crosspin 310.

The fin portions 334 of the crosspin 310 are comprised of a flexible material suitable to facilitate inward radial direction upon impacting the proximal surface 330. A suitable flexible material includes, but is not limited to, Lactosorb available from Biomet, Inc., of Warsaw Indiana or titanium for example. It is appreciated that the crosspin 310 may be formed with the flexible material as a unitary component. Alternatively, the fin portions 334 may be formed separately of flexible material and subsequently, or concurrently, mated with the intermediate portion 316 of the crosspin 310 having an alternate material. The crosspin 310 may be inserted into the femoral tunnel 24 in accordance with the teachings set forth above, or may be used in cooperation with other techniques for locating a soft tissue replacement 86 over the surface of the crosspin 310 in a femoral tunnel 24.

Figure 19:
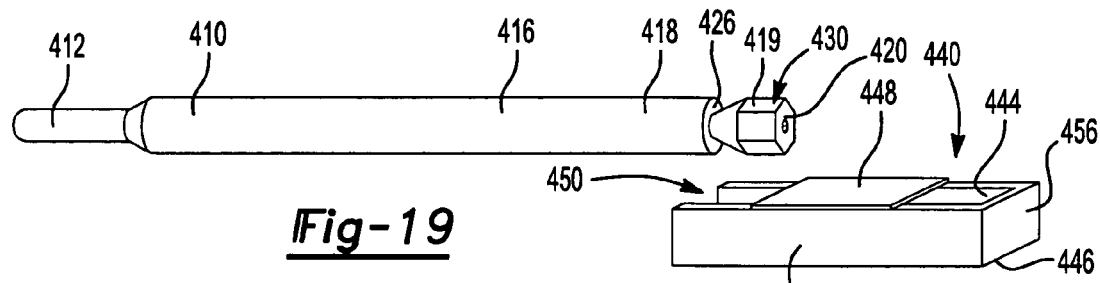
FIG. 19 is a perspective view of a crosspin according to additional features shown with a driver.
Figure 20:
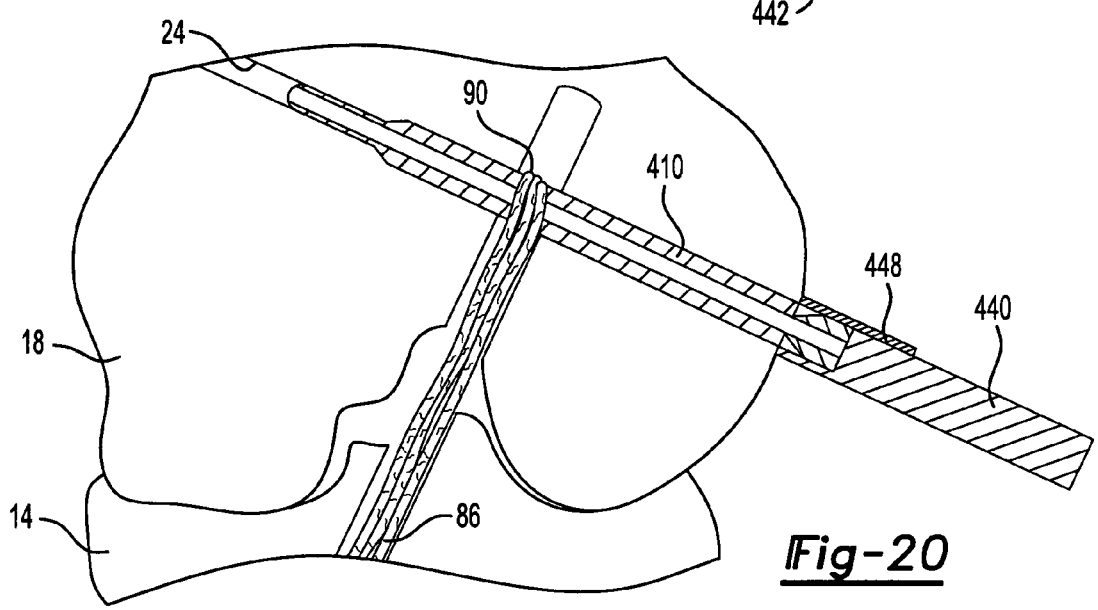
FIG. 20 is a sectional view of the crosspin and driver of FIG. 19 shown with the crosspin inserted into a desired location in the femoral tunnel.
Figure 21:
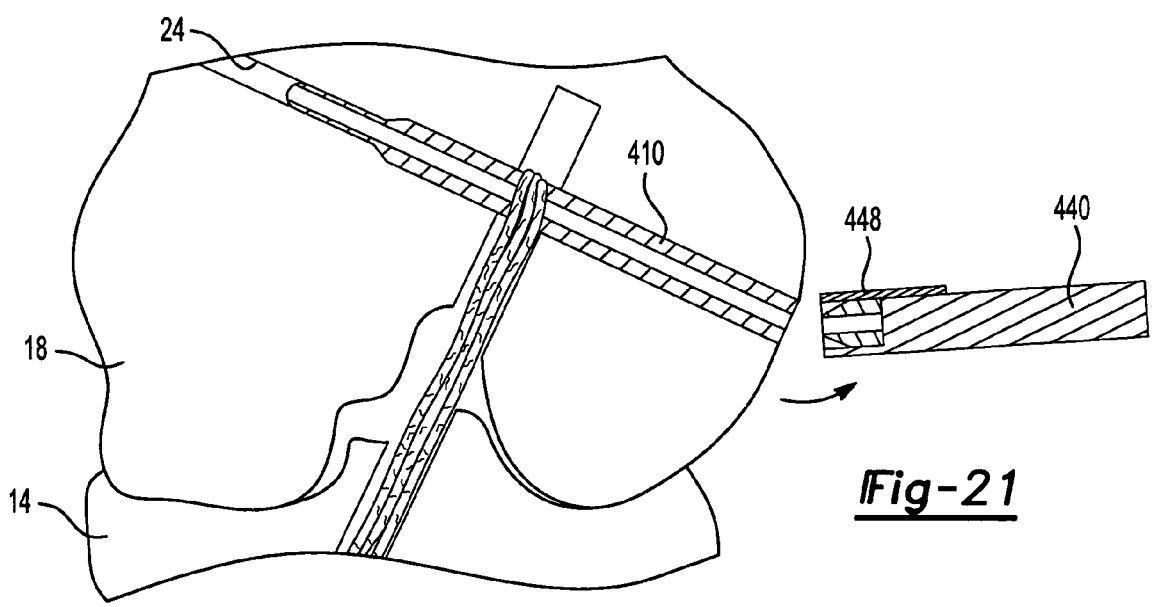
FIG. 21 is a sectional view of the crosspin and driver of FIG. 20 shown with a proximal portion of the crosspin disconnected from the body of the crosspin.

With reference now to FIGS. 19-21 a crosspin and system for inserting the crosspin 410 according to other features will be described. The crosspin 410 generally includes a distal tip portion 412, an intermediate portion 416, a proximal portion 418 and a breakaway portion 419 having a breakaway end 420. As will be described, the breakaway portion 419 is adapted to be disconnected from the proximal portion 418 upon locating the crosspin 410 at a desired depth into the femoral tunnel 24.

The crosspin 410 transitions from the proximal portion 418 to the breakaway portion 419 at an intersection area 426. As will be described, the breakaway portion 419 is disconnected from the proximal portion 418 at the intersection area 426. The breakaway portion 419 tapers inwardly from an engagement surface 430 toward the intersection area 426. The engagement surface 430 is adapted to be matingly received by a driver 440.

The driver 440 generally includes a first engaging wall 442, a second engaging wall 444, a third engaging wall 446 and a fourth engaging wall defined by a slidable cover portion 448. The breakaway portion 419 of the crosspin 410 is adapted to be inserted into the driver 440 through an access passage 450. The cover portion 448 is subsequently closed over the breakaway portion 419 of the crosspin 410 thereby capturing the breakaway portion 419 in the driver 440. It is appreciated that the cover portion 448 may alternatively be a stationary wall whereby the breakaway portion 419 of the crosspin 410 may be inserted axially into an opening defined opposite an end wall 456. The driver 440 is adapted to impose rotational movement onto the breakaway portion 419 if desired during insertion of the crosspin 410 into the tunnel 24. Accordingly, the engagement surface 430 defines a hexagonal surface for mating with the engagement walls 442-448 of the driver 440. It is appreciated however, that other complementary engagement surfaces may be employed on the proximal portion 418 and the driver 440. Furthermore, it is appreciated that a conventional nut driver may similarly be employed.

Once the driver 440 locates the crosspin 410 at a desired location in the femoral tunnel 24 (FIG. 20), the breakaway portion 419 is ready to be disconnected from the crosspin 410. The crosspin 410 is formed as a unitary piece by any suitable biocompatible material. In this regard, a force is imposed onto the driver 440 causing the breakaway portion 419 of the crosspin 410 to fracture or shear from the intermediate portion 416 (FIG. 21). It is appreciated that the breakaway portion 419 may alternatively be formed as a separate component and joined to the proximal portion 418 of the crosspin 410 by any suitable mechanical or chemical fastening techniques. The disconnecting force imposed by the driver 440 in that regard must be adequate to overcome the mechanical or chemical fastening to disconnect the breakaway portion 419 of the crosspin 410 from the proximal portion 418. It is also appreciated that while the breakaway portion 419 of the crosspin 410 is described as cooperating with the driver 440, the crosspin 410 alternatively may be urged into the femoral tunnel 24 by the insertion member 110 (FIG. 12) according to the teachings above and subsequently sheared from the proximal portion 418 by an impact force such as imparted by the impacting instrument 130 (FIG. 13). Furthermore, the crosspin 410 may be located into the femoral tunnel 24 by any suitable method and the breakaway portion 419 be disconnected by any method such as with the impacting instrument 130.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, the specification and the following claims.

What is claimed is:

1. A system for securing a soft tissue replacement in a bone tunnel comprising:
    a crosspin, comprising:
        a proximal end defining a recess having an arcuate shape;
        a distal tip portion;
        an intermediate portion transitioning from said distal tip portion at a ramp portion and the distal tip portion extends coplanar with an outer sidewall of the intermediate portion;
        a longitudinal slot defined by said intermediate portion and having a depth extending from a first outer longitudinal surface to a terminal longitudinal surface, said depth having a distance greater than half of a width of the crosspin, said terminal longitudinal surface defining a terminal axis, wherein said terminal axis is offset from and substantially parallel to an axis defining a centerline of a longitudinal axis of the crosspin, wherein said longitudinal slot is defined by opposing side walls, which each extend for a distance greater than half of said width of the crosspin;
    a flexible member extending longitudinally through said longitudinal slot; and
    a driver having a proximal end and a distal end, the driver having a neck portion extending from said distal end of said driver and an eyelet extending from a distal end of said neck portion, said eyelet matingly engaging the proximal end of said crosspin such that said eyelet is received in said arcuate recess to enable said driver to drive said crosspin into an engaged position whereby the soft tissue replacement is in a secure relationship with the bone, wherein an end of said flexible member is attached to said eyelet.

2. The crosspin of claim 1 wherein said distal tip portion is offset from said longitudinal axis of the crosspin and extends from a second longitudinal surface to said terminal longitudinal surface, said terminal longitudinal surface laterally offset between said second outer longitudinal surface and said centerline of the crosspin.

3. The crosspin of claim 1, wherein the longitudinal slot extends from the distal tip portion to a terminal location at an end of the crosspin.

4. The system of claim 1, wherein the end of said flexible member is directly attached to said eyelet.

5. A system for securing a soft tissue replacement in a bone tunnel comprising:
    a crosspin defining a longitudinal cannula extending through the crosspin between a proximal end and a distal end and adapted to be inserted into a transverse femoral tunnel and support the soft tissue replacement;
    a first flexible member extending through said longitudinal cannula; and an insertion member having a distal end secured to said first flexible member, the insertion member including a neck portion that defines a shoulder, the neck portion adapted to be received within the femoral tunnel a predetermined distance so that the neck portion abuts the bone when the crosspin is in the engaged position, the insertion member defining an eyelet protruding from a distal end of said neck portion and an end of said first flexible member is coupled to said insertion member at said eyelet and pulled through said transverse femoral tunnel, said eyelet extending transverse to said longitudinal cannula; and wherein the distal end of the insertion member matingly engages a proximal end of said crosspin such that said eyelet is received in a recess or the longitudinal cannula of said crosspin to enable said insertion member to push said crosspin into an engaged position whereby the soft tissue replacement is in a secure relationship with the bone.

6. A system for inserting a crosspin into a bone tunnel comprising:

a crosspin having a distal portion, an intermediate portion, a proximal portion extending from said intermediate portion and a breakaway portion detachably coupled to an end of said proximal portion and operable to be disconnected from said proximal portion, said breakaway portion defining a terminal proximal end of said crosspin when coupled thereto;

a driver having a proximal end, a distal end and planar outer walls extending therebetween that define a passage, said breakaway portion being received in said passage at said distal end of said driver such that said passage substantially surrounds and cooperates with said breakaway portion and said proximal end of said driver extends beyond said terminal proximal end of said crosspin, the planar outer walls including a pair of parallel spaced apart side walls and a bottom wall connecting said parallel side walls; and a slidable cover portion that slides relative to said pair of parallel spaced apart walls so as to slide over said breakaway portion and cooperate with said planar outer walls to enclose said breakaway portion within said driver, said driver imposes a force onto said breakaway portion that causes said breakaway portion to disconnect from said proximal portion;

wherein said slidable cover portion extends parallel to said bottom wall along only one side of said driver.

7. The system of claim 6 wherein said breakaway portion defines an engagement surface for matingly receiving a complementary engagement surface on said driver.

8. The system of claim 7 wherein said breakaway portion tapers inwardly from said engagement surface toward said proximal portion.

9. The system of claim 6 wherein said slidable cover portion is slidable from a first position to a second position, such that in the first position said breakaway portion is exposed and in the second position, the slidable cover portion is disposed over said breakaway portion and captures said breakaway portion within said driver.

10. The system of claim 6, wherein said breakaway portion includes a hexagonal shaped engagement surface for mating with the pair of parallel spaced apart side walls, the bottom wall, and the slidable cover portion of the driver.

\* \* \* \* \*

UNITED STATES PATENT AND TRADEMARK OFFICE
CERTIFICATE OF CORRECTION

| | | |
|---|---|---|
| PATENT NO. | : 8,002,778 B1 | Page 1 of 1 |
| APPLICATION NO. | : 10/878559 | |
| DATED | : August 23, 2011 | |
| INVENTOR(S) | : Jason D. Meridew | |

It is certified that error appears in the above-identified patent and that said Letters Patent is hereby corrected as shown below:

Column 5,
Line 42, after "may" insert --be--.

Column 6,
Line 66, after "Warsaw" insert --,--.

Signed and Sealed this
Twenty-second Day of November, 2011

David J. Kappos
*Director of the United States Patent and Trademark Office*